(12) United States Patent
Yu et al.

(10) Patent No.: US 7,989,396 B2
(45) Date of Patent: Aug. 2, 2011

(54) BIOMOLECULE IMMOBILIZATION ON BIOSENSORS

(75) Inventors: Heng Yu, Mountain View, CA (US); Nader Pourmand, San Mateo, CA (US); Shan X. Wang, Portola Valley, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 638 days.

(21) Appl. No.: 11/949,442

(22) Filed: Dec. 3, 2007

(65) Prior Publication Data
US 2008/0161200 A1     Jul. 3, 2008

Related U.S. Application Data

(60) Provisional application No. 60/872,808, filed on Dec. 5, 2006.

(51) Int. Cl.
    *C40B 50/18*     (2006.01)
    *C40B 60/02*     (2006.01)

(52) U.S. Cl. ............................................. 506/32; 506/34
(58) Field of Classification Search .................... 506/32, 506/34
See application file for complete search history.

(56) References Cited

U.S. PATENT DOCUMENTS

| 5,445,934 | A | | 8/1995 | Fodor et al. | |
|---|---|---|---|---|---|
| 5,582,697 | A | | 12/1996 | Ikeda et al. | |
| 5,624,711 | A | * | 4/1997 | Sundberg et al. | 506/32 |
| 5,981,297 | A | | 11/1999 | Baselt | |
| 6,197,503 | B1 | | 3/2001 | Vo-Dinh | |
| 6,391,937 | B1 | | 5/2002 | Beuhler et al. | |
| 6,770,489 | B1 | | 8/2004 | Enpuku et al. | |
| 6,800,331 | B2 | * | 10/2004 | Bilyk et al. | 427/387 |
| 7,022,379 | B2 | | 4/2006 | Winterton et al. | |
| 7,026,014 | B2 | | 4/2006 | Luzinov et al. | |

OTHER PUBLICATIONS

Wang, Shan X., Bae, Seung-Young, Li, Guanxiong, Sun, Shouheng, White, Robert L., Kemp, Jennifer T., Webb, Chris D., Towards a magnetic microarray for sensitive diagnostics, Journal of magnetism and Magnetic Materials 293, 2005, pp. 731-736.
Minard-Basquin, C., Chaix, C., Pichot, C., The use of (oligonucleotide-maleic anhydride copolymer) conjugates in nucleic acid diagnostic assays: effect of the number of oligonucleotides per polymer on test sensitivity improvement, Nucleosides, Nucleotides & Nucleic Acids, 20(4-7), 2001, pp. 895-899.
Pompe, Tilo, Renner, Lars, Werner, Carsten, Nanoscale features of fibronectin fibrillogenesis depend on protein-substrate interaction and cytoskeleton structure, Biophysical Journal, Jan. 2005, pp. 527-534, vol. 88(1).
Umeharra, "Current Rectification with Poly-L-Lysine-Coated Quartz Nanpipettes," Nano Letters, vol. 6, No. 11, 2486-2492, published Oct. 5, 2006.
Pompe, et al., Maleic Anhydride Copolymers—A versitile Platform for Molecular Biosurface Engineering, Biomacromolecules 4:1072-1079 (2003).
Felthouse, et al., Maleic Anhydride, Maleic Acid, and Fumaric Acid, Huntsman Petrochemical Corporation, submitted for Kirk Online, 2001.
Lee, et al., Chemically-specific probes for the atomic force microscope, Israel J. Chem. 36, 81-87 (1996).

* cited by examiner

*Primary Examiner* — Amber D. Steele
(74) *Attorney, Agent, or Firm* — David J. Aston; Peters Verny, LLP

(57) ABSTRACT

A highly specific and versatile surface chemistry for immobilization of amine-terminated probes is disclosed. A bi-layered polymer thin film serves as the platform for coupling the probes, which are preferably oligonucleotides. The process involves sequentially coating a substrate with polyamine and polyacid anhydride. Hydrolyzed polyacid anhydride groups may be converted to non-hydrolyzed groups at about 100° C. prior to probe attachment. The process of coating the substrate requires no harsh chemical pretreatment of substrates such as RCA or Piranha cleaning. In addition, simple thermal activation of the anhydride groups has a low requirement for storage, leading to a long shelf life of modified surfaces. The disclosed surface chemistry is especially compatible with microfabrication processes, and its effective application to magnetic biosensors is demonstrated.

26 Claims, 6 Drawing Sheets

6A

6B

BIOMOLECULE IMMOBILIZATION ON BIOSENSORS

CROSS-REFERENCE TO RELATED APPLICATIONS

This Application claims priority to U.S. Provisional Patent Application No. 60/872,808, filed Dec. 5, 2006, which is incorporated herein by reference.

STATEMENT OF GOVERNMENTAL SUPPORT

This invention was made with U.S. Government support under NIH Grant POI-HG00025, NIH IU54CA119367-01, and DARPA grant N000140210807. The U.S. Government has certain rights in this invention.

REFERENCE TO SEQUENCE LISTING, COMPUTER PROGRAM, OR COMPACT DISK

Applicants assert that the paper copy of the Sequence Listing is identical to the Sequence Listing in computer readable form found on the accompanying computer disk. Applicants incorporate the contents of the sequence listing by reference in its entirety.

BACKGROUND OF THE INVENTION

1. Field of the Invention

The present invention relates to the field of surface modification of a substrate so that a biomolecule may be attached to it.

2. Related Art

3. Background

The attachment of biomolecules on a suitable surface has found a variety of bioanalytical applications such as in microarrays, biochemical sensors, etc. In a biological microarray system, "probe" biomolecules such as polynucleotides, oligonucleotides, proteins or peptides are immobilized on a suitable surface. These probes are used to capture other biomolecules ("targets") that can recognize the probes. For example, in a DNA microarray, immobilized probe polynucleotides or oligonucleotides hybridize to complementary target DNA or DNA fragments in solution, providing sequence information for the targets that can be used to monitor gene expression, map genes, identify bacteria etc. In an immunoarray, immobilized protein antibody or antigen is used to bind to a specific antigen or antibody, respectively, thus making it possible to detect proteins of clinical interest through detection of their binding to the cognate probe.

It is clear that for applications such as those mentioned above, one crucial requirement is appropriate immobilization of probes on a suitable substrate. During the last two decades, a large number of approaches have been developed for immobilization of different biomolecular probes. These strategies may be categorized as pre-synthesized or on-site synthesized, depending on whether the probes are synthesized or extracted and then immobilized on the substrate, or synthesized directly on the substrate.

Pre-synthesized probes are generally either natural products extracted from biological entities or chemically synthesized in a lab; on-site synthesis mainly refers to the solid-phase synthesis of oligonucleotides on an array substrate, such as disclosed in U.S. Pat. No. 5,445,934, issued to Fodor et al. on Aug. 29, 1995, entitled "Array of oligonucleotides on a solid substrate." In this patent, a photosynthesis strategy is applied to synthesize oligonucleotide probes with different sequences on a glass slide. This patent discloses that linker molecules can be attached to the substrate via carbon-carbon bonds using, for example, (poly)trifluorochloroethylene surfaces, or preferably, by siloxane bonds (using, for example, glass or silicon oxide surfaces). Siloxane bonds with the surface of the substrate may be formed in one embodiment via reactions of linker molecules bearing trichlorosilyl groups.

Methods for immobilizing pre-synthesized probes onto a solid substrate fall into two categories: covalent attachment and simple adsorption. Adsorption of probes onto substrates often takes advantage of electrostatic attraction between substrates and probes. For example, a glass is generally negatively charged when in a neutral or basic solution. It can then adsorb positively charged amine polymers. The polyamine can in turn serve as a support to adsorb other negatively charged probes such as oligos or many proteins. In general, however, simple adsorption does not provide strong enough attachment and thus covalent interaction between substrate and probes is required. One exception of noncovalent adsorption is the strong interaction between biotin and streptavidin, which has been applied for attaching different probes. For example, biotin-labeled probes can be immobilized to streptavidin-modified substrates and form a strong attachment. However, this scheme also requires efficient, strong binding between streptavidin and the substrate.

In reality, covalent attachment of probes onto substrates is more reliable and adopted more often. For covalent attachment, the substrates are modified with suitable reactive groups or linkers for probes; at the same time, the probes carry groups reactive toward the modified substrates and so can form covalent bonds with the reactive groups on the substrates. Modification of substrates with different reactive groups has been well documented. These groups include hydroxyl, carboxyl, amine, aldehyde, hydrazine, epoxide, etc. The modified substrates can then be used to constitute arrays such as DNA or protein microarrays for capturing DNA or protein of interest.

One concern in the modification of substrates is the efficiency of capturing target molecules by probes immobilized on the substrates. When the probes are bound on a flat substrate, the steric crowding between the probes is thought to be responsible for low capture efficiency as observed in some arrays. One strategy to overcome this shortcoming is to bind the probes in a 3D substrate or a substrate modified with a 3D support. Application of 3D polymer matrices for immobilizing probes has been disclosed in U.S. Pat. No. 6,391,937, issued to Beuhler et al. on May 21, 2002, entitled "Polyacrylamide hydrogels and hydrogel arrays made from polyacrylamide reactive prepolymers." As disclosed there, a hydrogel of either polyacrylate or urea containing reactive groups for probes is deposited onto glass substrates.

U.S. Pat. No. 7,026,014, issued to Luzinov et al. on Apr. 11, 2006, entitled "Surface modification of substrates," discloses a process that includes applying polymer comprising multiple epoxy groups and having a molecular weight of at least about 2000 to the surface of a substrate. Other epoxy groups in the anchoring layer, not utilized in forming the layer, may be used to graft surface modifying materials to the surface. For instance, macromolecules, biomolecules, polymers, and polymerization initiators may be grafted to the surface via the anchoring layer.

Pompe, et al., "Maleic Anhydride Copolymers—A Versatile Platform for Molecular Biosurface Engineering," *Biomacromolecules* 4:1072-1079 (2003) discloses the use of different maleic anhydride copolymers such as PEMA, poly (ethylene-alt-maleic anhydride), which were covalently bound to $SiO_2$ surfaces. The copolymer solutions were applied to substrate surfaces which had been freshly oxidized and thereafter surface modified with 3-aminopropyl-dimethylethoxy-silane. Stable covalent binding of the polymer films was achieved by annealing at 120° C. for generation of imide bonds with the amino-silane on the $SiO_2$ substrate. Amino functionalization of the substrates was achieved on $SiO_2$ surfaces by silanization. Polymer substrates were amino-functionalized by low-pressure plasma treatment in ammonia atmospheres. Biomolecules (e.g., fibronectin) were attached to the maleic anhydride copolymers through reactivity of the anhydride function toward amines. This process uses an amino-silane, and does not suggest the use of a polyamine. As a silanization process, such a method involves organic solvents and may have variable results due to reproducibility problems in the process.

The present methods and materials have particular application to microarrays of nucleic acid or peptide probes immobilized on a substrate, and particularly to microarrays which employ structures added after the polymer surface treatment, such as would be added by etching and/or photolithography in a microfabrication process.

DNA microarrays have become essential devices in molecular biology as they allow high-throughput analysis of transcriptional profiling (REF 1) and medical diagnostics (REF 2). The success of DNA microarrays has also inspired a recent trend of combining microelectromechanical systems (MEMS) with biomolecules (BioMEMS). By integrating microarrays and detection systems into a miniaturized single device, BioMEMS has the potential to revolutionize the future practice of medicine and health care (REF 3). Surface chemistries developed for conventional microarrays, however, are not easily adopted in these BioMEMS systems. The incompatibility of biomolecules and microfabrication is caused mainly by two factors. First, the microfabrication process often involves elevated temperatures and harsh chemical and physical treatments that can denature or damage biomolecules; second, DNA immobilization chemistries always start with a strong acid cleaning such as Piranha or a strong base cleaning such as RCA to activate the substrates, a harsh condition that the components (e.g., sensors) of a MEMS device can rarely survive. It is thus very challenging to integrate biomolecules into common microfabrication processes (REF 4).

BRIEF SUMMARY OF THE INVENTION

The following brief summary is not intended to include all features and aspects of the present invention, nor does it imply that the invention must include all features and aspects discussed in this summary.

In one aspect, the present invention provides a method of linking biomolecules to solid supports, or substrates (e.g., glass or $SiO_2$), using layers of polymers for covalent attachment of the biomolecules. In a first step, molecules or polymers bearing amine groups are introduced onto the solid substrates; amine reactive polymers are then coated onto the amine modified substrates. The immobilized amine reactive polymer film can then be used to couple biomolecules having amine groups, such as amino-oligos or proteins with amine side chains, such that the reactive groups on the polymer serve as a linking reagent between the biomolecules and the solid substrate. A preferred method is to attach an amino-modified oligonucleotide directly to an activated anhydride polymer. The preferred process uses an aqueous solution of partially hydrolyzed polymer obtained by heating a low concentration (e.g., 2%, or less than 10%) of the anhydride suspension in water. Hydrolysis is necessary to make an aqueous solution since non-hydrolyzed polymer is not soluble in water. Once the partially hydrolyzed polymer is coupled, it can be converted to a non-hydrolyzed polymer again by heating. Heating may be done at a relatively low temperature, e.g., about 90-110° C., or as high as 200° C., but preferably e.g., at about 100° C. Thus, the preferred process is very clean and simple and does not require toxic organic solvents.

In certain aspects, the present invention comprises a method for preparing a substrate for use in a biosensor, where the biosensor will have biomolecules such as proteins or polynucleic acids immobilized on the sensor. One first provides a substrate having an oxide surface that is reactive with a primary amine; such a surface may, e.g., be a native oxide surface such as found on a silicon chip. One then coats the substrate surface with a molecule containing a primary amine to form a polyamine covalently linked to the substrate. One then contacts the polyamine with a polyacid anhydride having multiple acid anhydride groups, such that one portion of the polyacid anhydride binds to the bonded polyamine and another portion of the polyacid anhydride is retained for linking to biomolecules. This is illustrated in FIG. 1, where it is seen that the illustrated polyacid anhydride, poly(ethylene-alt-maleic acid), binds with some of its —COO— groups to the amine surface, and some of its COO— groups remain free for later reaction with the biomolecules.

The polyacid anhydride may be partially hydrolyzed, i.e., having some acid and some anhydride groups, as illustrated in FIG. 1 prior to heating. Partial hydrolysis is judged by solubility, but preferably ranges, e.g., between about 10% and 90% acid groups. The method may further comprise a step of dehydrating (e.g. heating to 100° C., or about 90-200° C.) the partially hydrolyzed polyacid anhydride to a corresponding polyanhydride, which then may be readily reacted with an amine-containing biomolecule. In certain embodiments, the partially hydrolyzed polyacid anhydride is a copolymer of a dicarboxylic acid anhydride and a monomer. The monomer is preferably selected from the group consisting of ethylene, propylene, butene, butadiene, styrene, 1-octadecene and 1-tetradecene. The dicarboxylic acid anhydride is preferably selected from the group consisting of fumaric acid, itaconic acid, maleic acid, maleic anhydride, chloromaleic acid, dimethyl fumarate, chloromaleic anhydride, and mixtures and derivatives thereof.

The substrate may be provided with a variety of oxide groups, including, without limitation, $SiO_2$, $Al_2O_3$, $Ta_2O_5$ or $TiO_2$, for reaction with the amines to form the polyamine layer. Alternatively, the surface reactive with a primary amine may comprise sulfide groups.

The primary amine may be aqueous or may comprise an aminosilane, e.g., (3-aminopropyl) trimethoxysilane (APTMS) and N-(2-aminoethyl)-3-aminopropyl trimethoxysilane (EDA). The primary amine may form a self assembled monolayer, or may be a polyamine, such as PEI (poly(ethyleneimine), PAAm (polyallylamine), or poly-L-lysine (PLL).

The present invention further comprises a method for preparing a biosensor, in which a substrate having a surface reactive with a polyamine is coated with the polyamine in a process whereby one forms multiple, physically discrete areas of exposed polyamine, thus patterning the substrate. A polyacid anhydride is then linked to the exposed bonded polyamine. The preparation method may also include the step of dehydrating a partially hydrolyzed polyacid anhydride to a corresponding polyanhydride for ready reaction with an amine-functionalized biomolecule.

In certain other aspects, the present invention comprises a biosensor, comprising a substrate having thereon a polyamine layer, which is patterned to define separate, discrete physical areas of exposed polyamine; a polyanhydride layer bound to each discrete physical area of the exposed polyamine layer; and a plurality of probe biomolecules attached to the polyanhydride layer through an amine group on the biomolecule, whereby the probe biomolecules are attached as different populations in each discrete physical area. The present biosensor may also be made to include a magnetic layer in proximity to the substrate surface. The magnetic layer may, e.g., be a giant magnetoresistive layer just under the oxide layer. One may use fabrication techniques known in the semiconductor industry to form an array of sensors, each sensor being wire bonded for individual detection, and the sensor may be packaged in a chip configuration or package. The package may be standardized, and each chip may contain a large array of biosensors having a variety of probe molecules (e.g., DNA probes) attached thereto. A magnetic sensing apparatus may be provided for use with bead-labeled analytes, where the beads are magnetic or ferromagnetic particles.

BRIEF DESCRIPTION OF THE DRAWINGS

FIG. 3 (F) shows a plot of particle coverage (/μm2) vs. target concentration for both positive hybridization assays and negative controls, scale bar: 1 μm; FIG. 3 (G) is a schematic diagram showing the configuration of substrate, probe, target (biotinylated), and label (streptavidin (SA)-coated magnetic particle).

FIG. 4(B) is an SEM image of a target coated sensor with very good coverage of magnetic nanoparticles; FIG. 4(C) is an SEM image of a negative control sensor (i.e., not coated with target) with very little coverage of nanoparticles;

FIG. 6 (right) is a photograph of an assembled chip after it has been wire bonded.

DETAILED DESCRIPTION OF THE PREFERRED EMBODIMENT

Definitions

Figure 1:
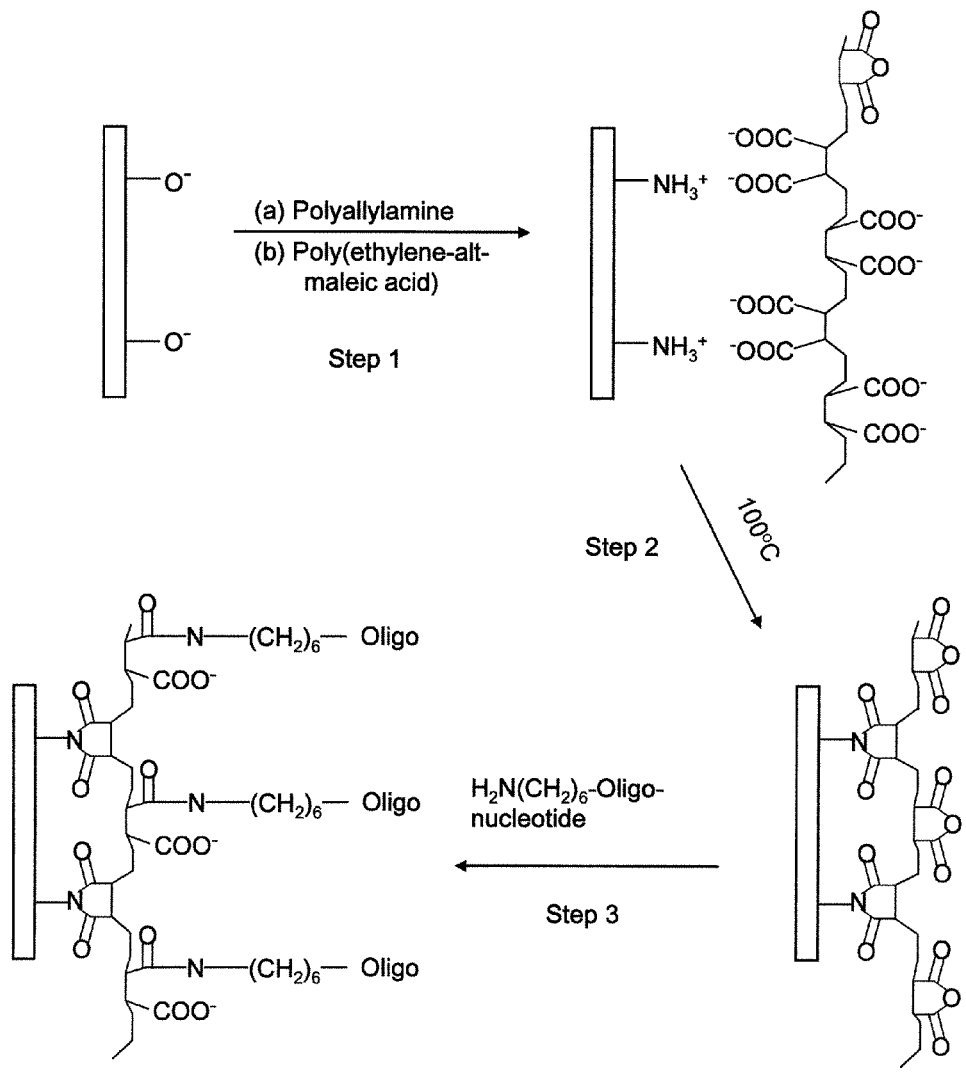
FIG. 1 is a reaction scheme showing a method of surface functionalization using polyallylamine and poly(ethylene-alt-maleic acid).

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

The term "probe" is used in its conventional sense to refer to a molecule that is immobilized onto a substrate for the purpose of capturing molecules of interest. For example, oligonucleotides can be attached to a substrate and hybridize and capture oligonucleotides or polynucleotides having complementary sequences. Probes are typically used in microarrays.

The term "native oxide surface" is used in its conventional sense to denote a surface on a substrate (e.g., silicon, aluminum or steel), which naturally oxidizes in the atmosphere.

The term "primary amine" is used in its conventional sense to denote a compound having a functionality of the formula —NH$_2$. The term "amine" includes primary, secondary, and tertiary amines according to the number of carbons bonded directly to the nitrogen atom.

The term "polyamine" means any polymer (i.e., having repeating units) that contains a reactive amine group. Of special interest are polymers containing primary amine groups such as PLL, PEI, PAAm, etc., since primary amines are more reactive toward anhydride groups.

The term "PEI" means polyethyleneimine, preferably according to the formula shown below:

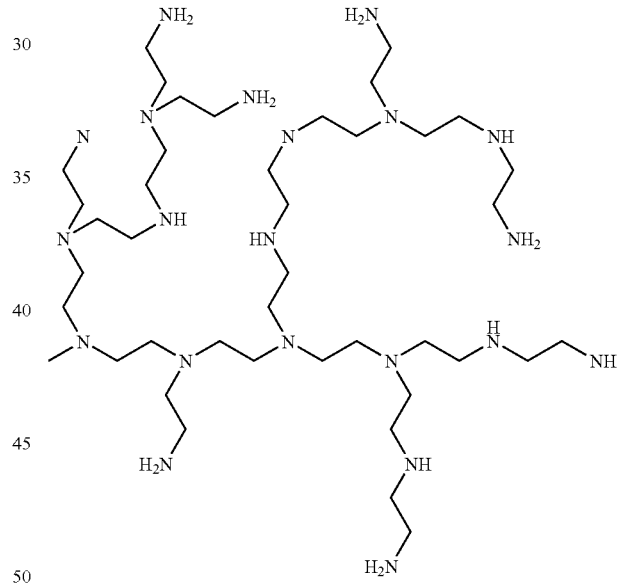

PEI comprises 25% primary amines, 25% tertiary amines, and 50% secondary amines.

The term "Polyallyl amine (PAAm)" means a polymer of the general formula shown below, including those structures such as described in U.S. Pat. No. 7,022,379, issued to Winterton et al. on Apr. 4, 2006, entitled "Single-dip process for achieving a layer-by-layer-like coating", where n is preferably about 100-1000.

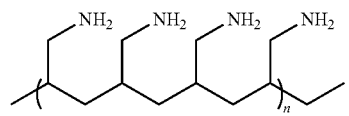

The term "Poly-L-Lysine (PLL)" means a compound of the formula below, where n is preferably about 100-1000.

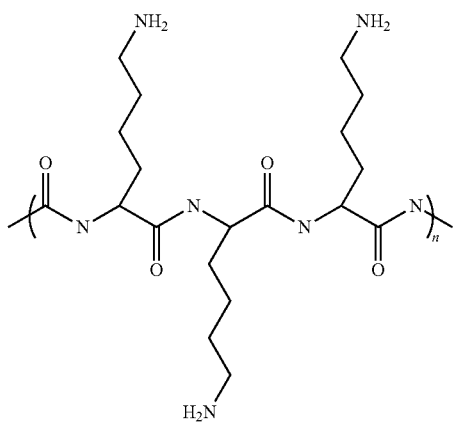

The term "polyacid anhydride" means any polymer that bears an anhydride group formed from two acid groups, where a portion of the groups in the polymer may be in either the acid or anhydride form. A preferred example is the maleic anhydride group, that is, an anhydride of cis-butenedioic acid (maleic acid), wherein carboxylic acid groups are next to each other in the cis form. Maleic anhydride has a cyclic structure with a ring containing four carbon atoms and one oxygen atom. Preferred anhydrides can be a homopolymer of maleic anhydride or copolymers of maleic anhydride with other monomers such as ethylene, propylene, butene, butadiene, styrene, 1-octadecene, 1-tetradecene, etc. Other copolymeric monomers include the group of monomers having at least one olefinic double bond, such as butene, pentene, hexene, octene, decene, butadiene, hexadiene, octadiene, cyclobutene, cyclopentene, cyclohexene, norbornene, norbornadiene, styrene and derivatives thereof. Preferred anhydride monomers are those from dicarboxylic acids, preferably α or β unsaturated C4 to C10 dicarboxylic acids, anhydrides or esters thereof, such as fumaric acid, itaconic acid, maleic acid, maleic anhydride, chloromaleic acid, dimethyl fumarate, chloromaleic anhydride, and mixtures thereof.

Sometimes the polymer is partially or completely hydrolyzed with the characteristic of two carboxylic acid groups right next to each other. These compounds are still referred to as polyanhydrides since an activation method is also incorporated for these hydrolyzed polymers in the surface modification process.

The term "substrate" means a solid surface that serves to support applied molecules. The modification of the substrate surface described in this invention could be applied to many substrates: $SiO_2$, glass, $Al_2O_3$, $Ta_2O_5$, polymer film etc.

The term "small molecule drug" means a traditional pharmaceutical compound, such as may be found in the Physician's Desk Reference, or PDR.net, or a compound in development for inclusion in that reference.

The term "magnetoresistive layer" means a layer of material that detects magnetic field signals by the resistance changes of a magnetic sensing element as a function of the amount and direction of magnetic flux being sensed by the element. One type of magnetoresistive (MR) sensor operates on the basis of the anisotropic magnetoresistive (AMR) effect in which a component of the resistance varies as the square of the cosine of the angle between the magnetization and the direction of current flow. These MR sensors operate on the basis of the AMR effect even though this effect produces only a relatively small percentage change in the resistance. In another MR type of sensor the resistance between two uncoupled ferromagnetic layers varies as the cosine of the angle between the magnetizations of the two layers and is independent of the direction of current flow. This mechanism produces a magnetoresistance that, for selected combinations of materials, is greater in magnitude than that for the AMR effect, and is referred to as "spin valve" (SV) or giant magnetoresistance.

DETAILED DESCRIPTION

Described below is a mild surface modification process for immobilization of DNA and other biomolecular probes onto substrates using thin polymer films. The described chemistry involves no harsh wet-chemical pretreatment for activating the substrate; furthermore, active functional groups for coupling probes are generated by simply heating the substrate to about 100° C. right before conjugation to form the reactive anhydride. Many different surfaces may be modified using the process of the current invention, including gold, silicon, etc.

The inventive mild surface chemistry has a great tolerance to the activity of substrates without requiring a harsh chemical treatment of the substrates. The chemistry preferably involves treatment with a polyacid-acid anhydride. The polyacid-modified substrate is neither moisture nor air sensitive—resulting in low storage requirements and a long shelf life. In addition, reactive cyclic anhydride groups can be regenerated by heating at 100° C. before coupling probes. Sensors made according to the present invention have high specificity and low background.

As a practical example, this mild surface chemistry may be applied to fabricate biomolecule (e.g., DNA) microarrays in magnetic biosensors, an emerging high-sensitivity BioMEMS device (REFs 5 and 6). Magnetic biosensors made according to the present invention show high specificity and very clean backgrounds in detecting hybridization events. In addition, the surface chemistry used to make these sensors is simple, with low storage requirements for modified substrates, and can be conveniently integrated into BioMEMS device fabrications.

1) Amine Coating

As the first step, an amine group is introduced onto the solid substrates. Many methods can be used for introducing amine groups to these substrates. For example, silanization of a glass substrate using APTMS (3-aminopropyl)trimethoxysilane-tetramethoxysilane), simple adsorption of PEI (poly (ethylene imine)) or other polymers onto the solid substrates, or plasma treatment of the substrates, especially polymer film with ammonium or other organic amine vapors, can all effectively introduce amine groups onto different substrates. The surface structure resulting from APTMS treatment is illustrated below.

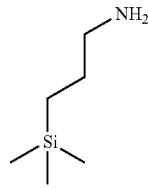

An alternative method employs another trialkoxyaminopropylsilane, particularly (3-aminopropyl)triethoxysilane (APTES, $H_2NCH_2CH_2CH_2-Si(OC_2H_5)_3$).

The method of choice for applying an amine layer is adapted to the particular substrate, whether solid, film or particles. A silanization process is widely used to modify oxide surfaces such as $SiO_2$, $Al_2O_3$, $Ta_2O_5$ and could easily introduce amine groups using silanizing reagents such as APTMS, etc. Another preferable method is deposition of amine containing polymers onto the solid substrates. Oxide surfaces are generally negatively charged when in contact with neutral solution, and their surface charge can be easily controlled by the pH of the contacting solutions. When the substrate is negative charged, generally positively charged amine polymers such as PEI, PLL, etc., are easily adsorbed onto the substrate. Briefly heating the substrate with adsorbed polymer can increase the adherence of polymer to substrate very effectively. Plasma treatment of the substrate with amine containing reagents can also effectively introduce amine groups. Finally, any other methods that can convert functional groups to amines are applicable here for the first step surface modification. Substrates are not limited to a solid surface or film, but could also be particle surfaces such as metal oxide colloids or polymer latex suspended in solvents. The surface modification method in the invention can be applied to any substrate after it is modified with amine groups.

Specifically exemplified below are two methods to introduce amine groups onto glass substrates: silanization and polyallyl amine adsorption.

An example of silanization presented here is to use APTMS in acetone as the coating solution for modification of a glass slide. The amine groups introduced are then reacted with polymers for the polymer immobilization.

Since a glass substrate is negatively charged when contacting with neutral solution, and amine polymers such as PEI, etc., are positively charged in the same condition, it is also advantageous to coat these polymers onto a glass surface. Amine groups attached to the polymer backbone are also used to react with poly anhydride and its copolymers. We found that briefly heating the PEI substrate at elevated temperatures greatly increases the binding of amine polymers to the substrates.

(2) Immobilization of Polyanhydride on the Amine Layer

The amine-bearing substrate is then coated with a polyanhydride polymer to form a very stable insoluble polymer matrix, via the formation of amide bonds between the anhydride group of the polymer and amine groups on the substrate surface.

As will be discussed below, the remaining amine reactive sites on the polymer (i.e., those which do not react with the substrate surface) are then available for covalently coupling biomolecules bearing amine groups using the same reaction between amine and anhydride groups. One advantage here is that no other modification is needed for coupling biomolecules, and the amine reactive groups of the polymer bind both the polymer itself and biomolecules onto the substrate.

Any polymer or copolymer containing groups reactive with amines could be selected for this purpose. Examples include polymaleic anhydride and its copolymers with styrene, ethylene etc, and polyacrylic acid and its copolymers. Maleic anhydride is very reactive toward amine and thiol groups, and polyacrylic acid can be activated via various ways to form amide bonds with amines. Polymaleic anhydride homo- or co-polymers are especially useful since these polymers are all low-cost and commercially available. Furthermore, these polymers already bear abundant reactive groups of maleic anhydride; no further modification of the polymers is needed for binding both amine modified substrate and amine-bearing biomolecules.

The polyanhydride polymers serve two purposes using the same reaction: to covalently link polymer to the previously prepared amine coated surface of the substrate, and to subsequently couple biomolecules to the polymer matrix through an amide bond. In the modification process, amine coated substrates are immersed into a solution containing the polymer for a period of time followed by washing and rinsing. After the substrates are dried, they can then be stored in acid form (prior to step 2 of FIG. 1) for later biomolecule immobilization.

The modified substrate contains two layers, an amine layer on the bottom and an anhydride layer on the top. In the case where the amine layer is covalently attached to the substrate, such as is formed via a silanization process, covalent binding of anhydride polymers is very robust. When polyamine is physically adsorbed onto the substrates, subsequent coating with polyanhydride will still form a robust three-dimensional network by covalently crosslinking the polymers with amide bonds. In both cases, therefore, very robust polymer films can be formed that will neither be destroyed in the following modification nor be dissolved by different solvents such as water or other solvents. This stable support is highly desirable for coupling biomolecules.

One concern is the availability of reactive anhydride groups for binding both the surface amine groups and biomolecules. Most polyanhydride copolymers are alternative polymers with about 40% to 60%, usually 50% of the constitute monomers being anhydride monomers. In practice, this is a very high concentration of reactive groups that is more than enough to serve the two purposes of binding to surface amines as well as biomolecules.

The present polyanhydride coating solutions contain appropriate solvents and polymers of anhydrides. The selection of solvent depends on the nature of the polymer. For example, DMF (N,N'-dimethylformamide) or DMSO (dimethyl sulfoxide) and THF (tetrahydrofuran) are good solvents for polyethylene maleic anhydride, DMF, toluene, and THF are good solvents for polystyrene-co-maleic anhydride, and acetone is a good solvent for polybutadiene-co-maleic anhydride, etc. The solution concentration used is generally in the range of 0.1 mg/ml to 1 mg/ml to prevent the polymer deposition from being too thick.

Anhydride groups are very susceptible to water or moisture, thus traditionally requiring a dry condition for both the solvents used and the storage of modified substrates. However, we found that a simple method may be used to overcome the strict requirement of dry, moisture-free conditions. When an anhydride polymer is hydrolyzed completely or partially, it becomes water-soluble. The hydrolyzed anhydride groups can then be simply reactivated back to anhydrides by heating the substrate to about 100-150° C. for a period of time, ideally 1 hour. Thus, anhydride polymer deposition can be carried out in water solution using partially or completely hydrolyzed anhydride polymers, which can then be deposited on an amine-containing surface, as shown in FIG. 1. In the case of a completely hydrolyzed anhydride, the compound shown in step 1 of FIG. 1 exists as a maleic acid, but upon heating, as shown in step 2, loses water to obtain the anhydride form, i.e., is no longer completely hydrolyzed. The structure resulting from step 1 can then be stored until one wishes to reactivate the hydrolyzed anhydride groups to regenerate the anhydride groups for probe attachment. This is shown in FIG. 1 as heating step 2. The application of a water solution instead of organic solvents in step 1, as well as the simple reactivation of anhydride groups at elevated temperatures, greatly simplifies the surface modification procedure and lowers the cost. Once the anhydride, which is highly reactive, is formed, an amine-terminated biomolecule, such as an oligonucleotide, is coupled to the anhydride coating, as shown in step 3.

Figure 2:
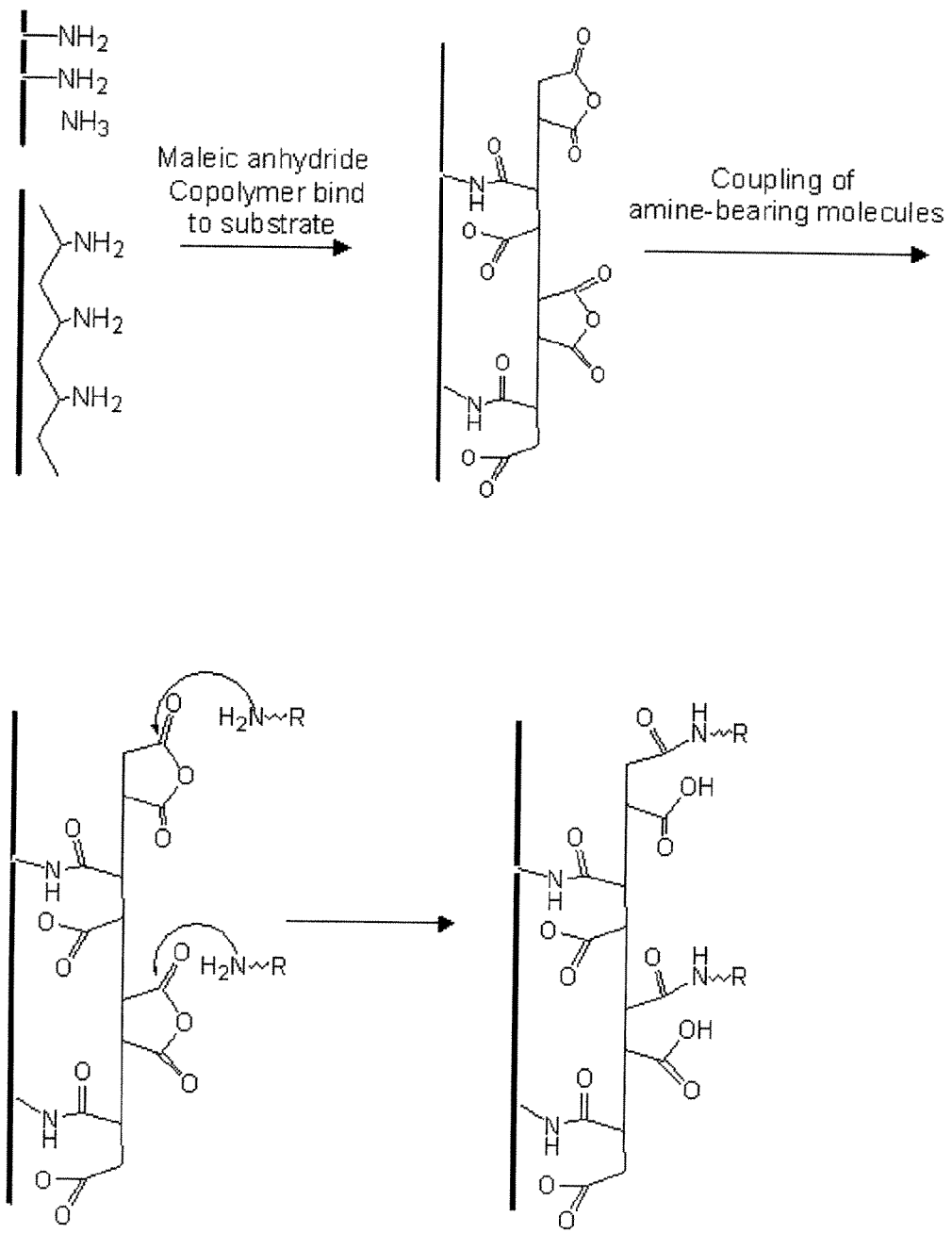
FIG. 2 is an alternative reaction scheme showing the reaction of amine-terminated probe molecules with a functionalized surface.

FIG. 2 illustrates an alternative embodiment of the process shown in FIG. 1. FIG. 1 shows in step 1 the addition of a polyacid anhydride, which is partially hydrolyzed, as shown by reactant (b) in step 1. That is, the poly(ethylene-alt-maleic acid (PEMA) that is illustrated has enough maleic anhydride groups hydrolyzed to render the material soluble in water, with one anhydride group shown. In contrast, in FIG. 2, the PEMA is in a dry solvent, namely DMF. The maleic groups are in the anhydride form without any group hydrolyzed. No heating step is necessary to convert groups to the anhydride form. FIG. 2 also shows a reaction mechanism for coupling biomolecules of the formula NH2~R. This mechanism is essentially a nucleophilic substitution, and is the same for the schemes in FIG. 1 and FIG. 2. The H2N~R is the same as the amine terminated oligonucleotide as in step 3 of FIG. 1, with the spacer group shown as a wavy line.

Figure 5:
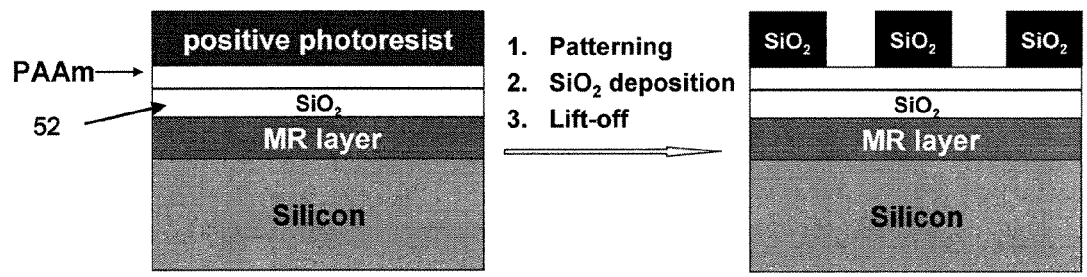
FIG. 5 is a schematic diagram showing sensor fabrication steps that expose PAAm on active sensor areas and coat a SiO$_2$ passivation layer on surrounding areas.

The covalent attachment to the substrate surface of the amine layer to a polyacid anhydride is impervious to subsequent processing steps, such as etching and photolithography, as shown in FIG. 5. The probes may thus be immobilized on areas that are physically separated by etched or deposited layers, or the substrate may be configured with other features added after the amine layer.

(3) Biomolecules (Probes) Immobilized on Polyanhydride

Shown below is a reaction between a maleic-anhydride-like polymer and a biomolecule having R1 and R2 groups, which vary depending on the nature of the biomolecule.

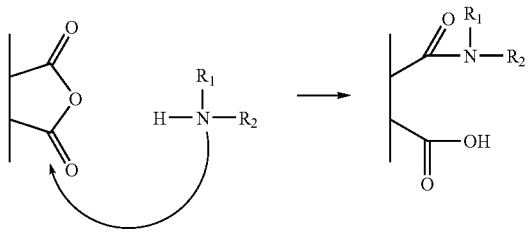

The above surface corresponds to the surface resulting from step 2 in FIG. 1 and can be seen as reacting in step 3. In this case the amine is a secondary amine, but in practice either primary or secondary amines can be used.

The polyanhydride surface resulting from step 2 (FIG. 1) can be applied to bind various amine-bearing molecules, especially to bind biomolecules such as oligonucleotides, polynucleotides, antibodies, aptamers, recombinant proteins, peptides, phages, etc. Oligos are synthetic oligonucleotides containing less than 60 oligonucleotides, in which an amine group is incorporated during the synthesis with a spacer (tether) group such as $C_6$ or $C_{12}$, or between $C_3$ and $C_{20}$. DNA has anhydride reactive amines on the bases that may be coupled to the poly anhydride substrate. Proteins can be coupled to the poly anhydride utilizing the terminal amine or pendent amine groups from amino acid side chains such as lysine, etc. The utility of these biomolecular probes on solid substrates has been well documented, such as in DNA microarrays, immunoarrays, or biosensors.

(4) Detection of Biomolecule (Target) Binding to Probe

Various detection schemes may be adapted to the present invention. In general, any detection system that is used with immobilized target molecules may be implemented with the present surface chemistry for binding of the target biomolecules to a substrate. In one aspect of the present invention, fluorescence is used to detect a binding event of a target to an immobilized probe. In this aspect, a fluorescent dye is used to label the target and is subsequently captured to the substrate together with the target. The detection of the target is then realized via scanning the fluorescence of the dyes.

In another example, U.S. Pat. No. 5,582,697, issued to Ikeda, et al. on Dec. 10, 1996, entitled "Biosensor, and a method and a device for quantifying a substrate in a sample liquid using the same," discloses a device which can quantify a substrate in a sample liquid by electrochemically measuring the amount of an electron acceptor that has been reduced by electrons generated in a reaction between the substrate and an oxidoreductase. U.S. Pat. No. 6,197,503 issued to Vo-Dinh, et al. on Mar. 6, 2001, entitled "Integrated circuit biochip microsystem containing lens," discloses a miniaturized biosensor as a biochip comprising multiple biological sensing elements such as DNA probes, excitation microlasers, a sampling waveguide equipped with optical detectors (fluorescence and Raman), integrated electrooptics, and a biotelemetric radio frequency signal generator.

Another aspect of the present invention involves the use of magnetically labeled targets. In this way, one may use SEM to visualize the target binding to the probes. Preferably, nanoparticles are chosen with a size larger than 10 nm for labeling the target since particles of this size are a good match to target molecules and can be easily visualized using SEM. The coverage of nanoparticles on the substrate can then determine the presence and concentration of targets. Alternatively, magnetically-labeled targets (e.g., super-paramagnetic particles, used in magnetoresistive-based biochips) may be detected using an integrated magnetic field sensor such as a giant magnetoresistive (GMR) multilayer, spin valve, AMR sensor, Hall effect sensor, etc.

A preferred embodiment of the present invention uses a magnetic sensor. In this case, the target biomolecule is labeled with a magnetic or ferromagnetic label. Its binding to the immobilized probe brings the label in proximity to the substrate, which contains an electrode whereby a change in resistance is measured.

A magnetic label may be detected by a SQUID device, as described in U.S. Pat. No. 6,770,489 issued to Enpuku on Aug. 3, 2004, entitled "Method for an immunoassay with a magnetic label and an apparatus for the same." There, (1) an analyte is labeled to detect antigen-antibody reaction, (2) the magnetic material label is magnetized by a magnetic field, and (3) the magnetized magnetic material label is detected by a SQUID, which detects a magnetic field having a right angle to the magnetic field.

A magnetic field may also be used to change the resistance of the area to which the target binds. See, e.g., U.S. Pat. No. 5,981,297 issued to Baselt on Nov. 9, 1999, entitled "Biosensor using magnetically-detected label." There, means are provided for magnetizing the attached label particles and detection means are used for monitoring the magnetic field sensors so as to detect the magnetic field produced by the presence of the attached magnetized label particles and thus the concentration of the target molecule is determined. A magnetic field generator creates a magnetic field that magnetizes the beads. The magnetic field generator can be an electromagnet, an air-cored wire coil, a straight wire, a conductive microfabricated trace, or a permanent magnet. Each magnetized bead generates a magnetic field that changes the resistance of the magnetoresistive element to which it is bound. A Wheatstone bridge is used to compare the resistance of the signal element with that of a reference element, which is located near the signal element and is identical to it, except that it lacks antibodies. The output of the Wheatstone bridge is converted to digital form; a microprocessor collects the resulting information and determines the total number of magnetized beads on the detector.

See also Ferreira et al., "Effect of spin-valve sensor magnetostatic fields on nanobead detection for biochip applications," *J. Appl. Phys.* 97, 10Q904 (2005). There, chips were set up in an experimental apparatus (further described by the authors in *Journal of Applied Physics* 93(10): 7281-7286 (1993)) and a planar electromagnet was used to create an in-plane uniform magnetizing field over the chips. Small volumes of a nanoparticle solution were placed over the chips and nanobead detection signals were measured in real time using a general-purpose interface bus controlled multimeter. Sensing currents of ±8 mA and external fields of −15, 0 and ±15 Oe were applied in order to elucidate the effects of the magnetostatic fields and the sense current field on label detection and to assess the best operating conditions for the detection of biomolecular recognition.

Further examples of different detection circuitry may be found in "Single magnetic microsphere placement and detection on-chip using current line designs with integrated spin-valve sensors: biotechnological applications", D. L. Graham, H. A. Ferreira, J. Bernardo, P. P. Freitas, J. M. S. Cabral, *J. Appl. Phys.*, vol. 91, pp. 7786-7788, 2002; "Detection of a micron-sized magnetic sphere using a ring shaped anisotropic magnetoresistnce based sensor: a model for a MR based biosensor", M. M. Miller, G. A. Prinz, S. F. Cheng, S. Bounnak, *Appl. Phys. Lett.*, vol. 80, pp. 4199-4201, 2002; "Detection of single magnetic microbead using a miniaturized silicon Hall effect sensor", P. A. Besse, G. Boero, M. Demierre, V. Pott, R. Popovic, *Appl. Phys. Lett.*, vol. 80, pp. 4199-4201, 2002; "A biochip based on a magnetoresistive sensor", J. Schotter, P. B. Kamp, A. Becker, A. Puhler, D. Brinkmann, W. Schepper, H. Bruckl, G, Reiss, *IEEE Trans. Magn.*, vol. 38, pp. 3365-3367, 2003, etc.

Particularly preferred is a device as described in Wang et al., "Towards a magnetic microarray for sensitive diagnostics," *Journal of Magnetism and Magnetic Materials* 293 (2005) 731-736, and in U.S. patent application Ser. No. 10/829,505, filed Apr. 22, 2004, and in U.S. patent application Ser. No. 11/297,883, filed Dec. 9, 2005, which are, as are the other references cited, incorporated herein by reference. As described there, spin valve sensor arrays were fabricated by photolithography and e-beam lithography with the following layers: Si/Ta 3 nm/Seed layer 4 nm/PtMn 15 nm/Co90Fe10 2 nm/Ru 0.85 nm/Co90Fe10 2 nm/Cu 2.3 nm/Co90Fe10 2 nm/Cu 1 nm/Ta 4 nm, (i.e., substantially similar to those used in the examples below). The pinned magnetic moment MP of the spin valve sensor was fixed in the −y direction and the free layer moment MF, which is along the x direction (perpendicular to the pinned layer magnetization), was rotated in response to an applied magnetic field Ha, which was swept in the y direction (in-plane detection mode). The resistance R of the SV sensor was measured using a four-probe or two-terminal method with the current-in plane (CIP) configuration. In the present device, changes in resistance will occur upon binding of appropriately labeled target molecules, e.g., having magnetic, super-paramagnetic or paramagnetic beads.

EXAMPLES

Materials and Methods

Polyallylamine hydrochloride (PAAm), polyethylene-alt-maleic anhydride (PEMA), PBS buffer (pH 7.4), Tween 20, 2-(N-Morpholino)ethanesulfonic acid (MES), Mercaptoundecanoic acid (MUA), and bovine serum albumin(BSA) were purchased from Aldrich and used as received (St. Louis, Mo.). Partially hydrolyzed PEMA aqueous solution is obtained by boiling a 2 wt % polymer in water suspension for ca. half an hour until a clear solution is obtained.

Photoresist SPR-3612 was from Shipley (Marlborough, Mass., USA). Magnetic nanoparticle (MACS) was from Miltenyi Biotec Inc. (Auburn, Calif.). Oligonucleotides were purchased from Integrated DNA Techonolgies Inc. (Coralville, Iowa) having the sequences of: positive probe: 5'-Amine-(CH2)6-CTA CCA ATC CAC AAA TAC CCA TCT ACC ATA-3'(SEQ ID NO: 1), negative probe: 5'-Amine-(CH2)-6-TTT TTT TTT TTT, (SEQ ID NO: 2) and target DNA: 5'-Biotin-TAT GGT AGA TGG GTA TTT GTG GAT TGG-3'(SEQ ID NO:3). SEM characterization of magnetic nanoparticles was done on an FEI XL30 Sirion SEM. A quartz mask was fabricated using a Micronic Laser Writer LRS-18. Optical lithography and patterning was performed using an Electronic Visions 620 Aligner.

Example 1

Chip Fabrication

As shown in FIG. 5, a silicon substrate containing an MR (magnetoresistance) layer was prepared as a spin valve. Spin valve magnetic sensors were fabricated from 4-inch silicon wafers containing layers Si/Ta 3 nm/seed layer 4 nm/PtMn 15 nm/Co90Fe10 2 nm/Ru 0.85 nm/Co90Fe10 2 nm/Cu 2.3 nm/Co90Fe10 2 nm/Cu 1 nm/Ta 4 nm with a magnetoresistance (MR) of 10.3% and a sheet resistance of 18.41Ω. Next, a silicon oxide layer 52 was added by sputter coating. This serves as a passivation layer and may be about 10-20 nm thick. Other passivation layers (e.g., silicon nitride or a combination of silicon oxide and silicon nitride) may be used.

Next, the prepared substrate having a thin $SiO_2$ passivation layer was coated with polyallylamine (PAAm) and heated at 170° C. for 2 min. A whole wafer was coated with PAAm by immersing the wafer into a 2 wt % PAAm in water solution for 30 seconds, rinsing with water, and blowing dry. The thickness of the polymer film was characterized by ellipsometry and found to be around 3 nm independent of polymer concentration or immersion time, which is characteristic of a self-limiting process (REF 7). It is also advantageous that this effective deposition step of a polyamine layer requires no strong chemical pretreatment of the $SiO_2$.

The wafer was then patterned such that polyamine was only exposed on an active sensor area. It was covered with a $SiO_2$ passivation layer on the remaining area. Conventional lithography methods were used to pattern the sensor surface exposed with active area coated with PMMa and the remainder with $SiO_2$ passivation layer. A layer of positive photoresist was applied to the PAAm layer. It was mask patterned and a layer of $SiO_2$ was applied. The unexposed areas were then lifted off, leaving physically discrete and separated areas of exposed PAAm.

Then, the exposed polyamine region was coated with partially hydrolyzed polyethylene-maleic anhydride (PEMA, which is a polyacid), as shown in step 1 of FIG. 1. This was obtained by immersing the chip into a 2 wt % partially hydrolyzed PEMA aqueous solution for 5 min, rinsing with water twice and blowing dry. In practice, the application of PEMA can be performed either before or after the whole wafer is diced into chips so that the chips may be activated on demand.

Figure 6:
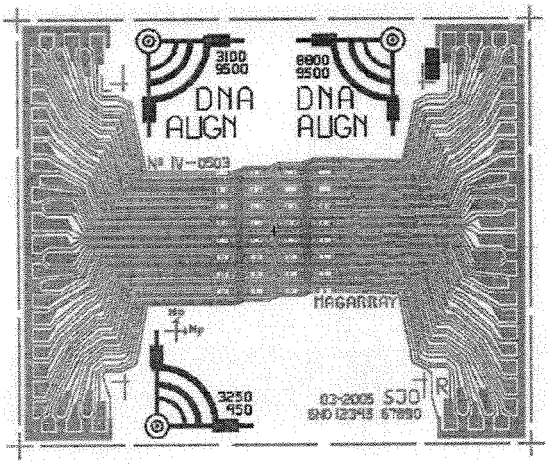
FIG. 6 (left) is a photograph of a layout of an example of a chip containing 64 sensors.
Figure 6:
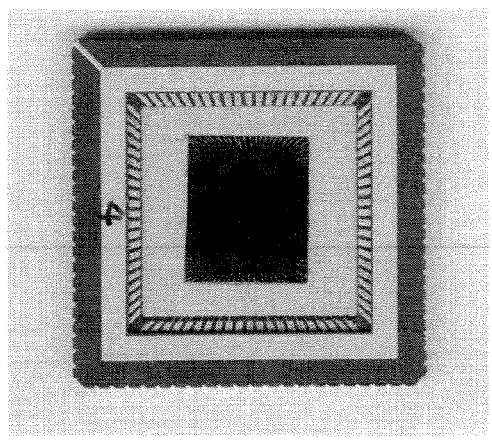

After the lift-off process shown as step 3 in FIG. 5, the whole wafer is protected with a layer of photoresist and diced into chips. Each chip contained 64 sensors that can be simultaneously monitored. The processed chip was then assembled and wirebonded. FIG. 6(A) shows the chip pattern, where eight rows of four spots each can be seen. The chip after wirebonding is shown in FIG. 6(B).

In the following activation step, step 2 of FIG. 1, the chips were heated at 100° C. for one hour to cyclize maleic acid groups. This activation step not only crosslinks and strengthens the underlying polyamine layer but also provides functional groups to covalently couple probe oligonucleotides bearing amino groups as shown in step 2 of FIG. 1. Additionally, compared to popular N-hydroxy-succinimide ester substrates that are prone to hydrolyze and may require EDC reactivation (REF 8), the simple thermal activation of polyacid surface does not impose as stringent storage requirements for modified substrates as the conventional method and gives the sensors a long shelf life.

Before oligonucleotide probe immobilization, the chip surface was activated by heating at 100° C. for 1 hour. After it was cooled down, 100 µM solutions of both positive and control probes were spotted on different sensors manually; the buffer used was PBS with a NaCl concentration of 1 M and the volume of each droplet was ca. 0.5 µL. After that, the chip was incubated overnight in a humidity chamber. Finally, the chip was blocked with 50 mM ethanolamine solution for 6 hours at room temperature; rinsed with PBS buffer (pH 7.4 solution contains 10 mM phosphate, 2.7 mM KCl and 137 mM NaCl) twice followed by water; and finally blown dry with argon. A magnetic particle solution was then applied to the chip to stain the chip for either SEM characterization or magnetic measurement. In the case of only SEM characterization, the chip was incubated with magnetic particle solution for 12 min followed by rinsing twice with PBS buffer (0.01% Tween 20), then briefly with water to remove salt. When magnetic measurement was performed, the signal was monitored in real time before, during, and after the incubation of magnetic nanoparticle solution.

Example 2

Hybridization Assays

Target hybridization was performed at room temperature under 100% humidity overnight in MES buffer (0.1 MES, 0.9M NaCl, pH 6.5). The chip was then rinsed with PBS buffer containing 0.01% Tween 20 three times, each for 1 min and finally blown dry with argon.

The general assay format for the present work is shown in FIG. 3(G). The probe is the oligo as shown in FIG. 1, attached to a substrate. The target DNA, if complementary, will bind to the probe, and bears a biotin label. This label is in turn tagged with a streptavidin-coated magnetic nanoparticle.

Hybridization assays were conducted on a duplex microarray (i.e., having two complete sets of probes) to demonstrate the performance of the present surface chemistry. Solutions of positive and control oligonucleotide probes bearing amino groups on the 5'-end were manually spotted to different sensors on the same chip following surface activation. The sensors were then blocked with ethanolamine and hybridized to target DNA complementary to the positive probe. The target DNA bears a biotin at the 5' end and can capture streptavidin (SA) coated magnetic nanoparticles via the biotin-SA interaction. Since the detection signal is directly related to the coverage of magnetic nanoparticles on the sensor surface, we used SEM to characterize the coverage and distribution of magnetic nanoparticles and study the dependence of nanoparticle coverage on target DNA concentrations.

Figure 3:
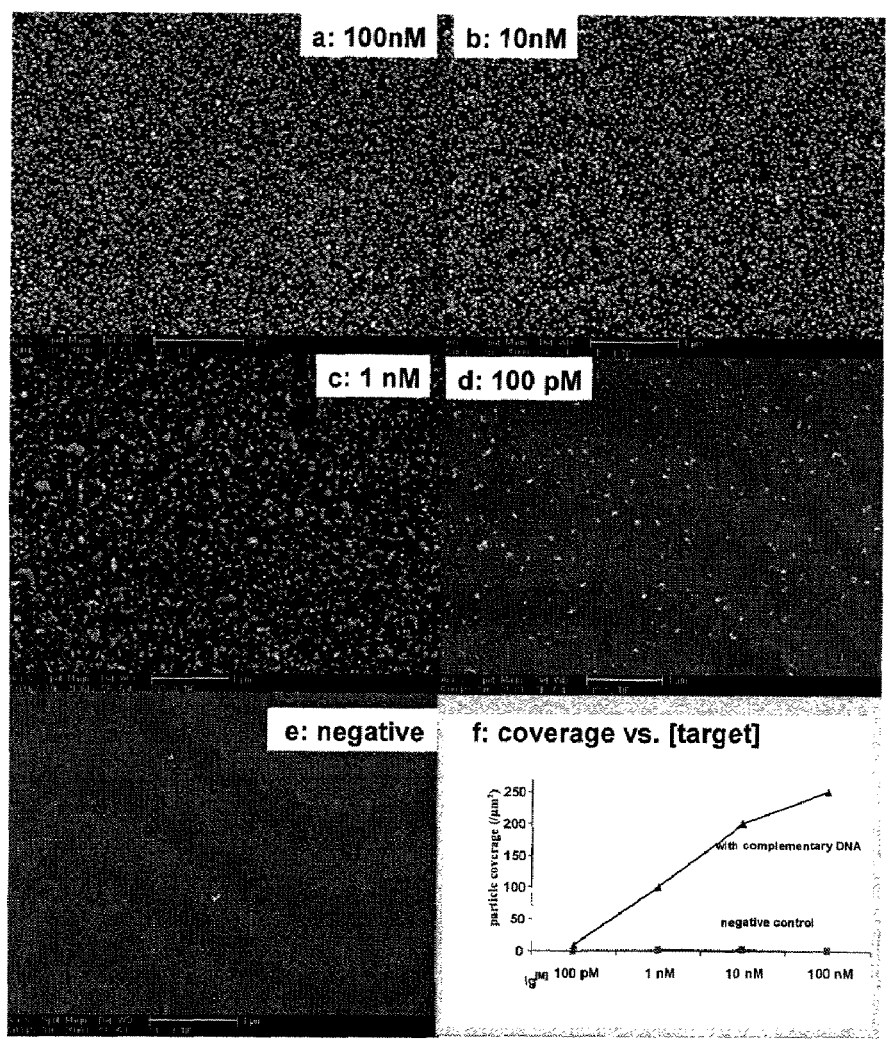
FIG. 3 (A-E) is a series of images showing magnetic particle coverage of different concentrations of target DNA: (A) 100 nM, (B) 10 nM, (C) 1 nM, (D) 100 pM, (E) negative control with 100 nM of target and non-complimentary probe.
Figure 3:
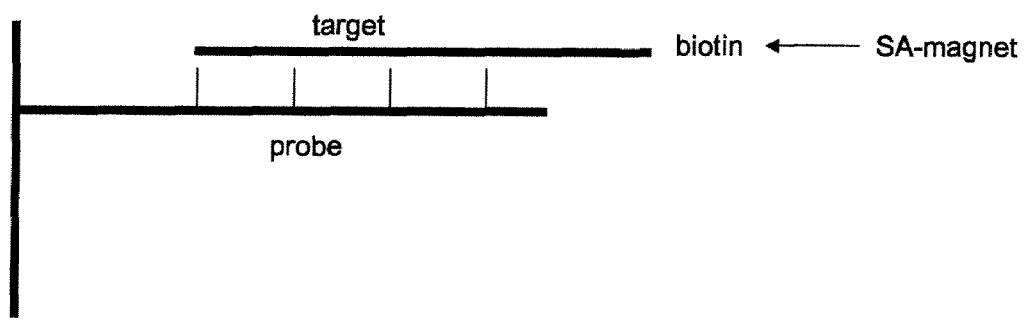

In this experiment, all target DNA was complementary to the probe, but was applied in different concentrations. The DNA sequences used were the same as in Example 3. As shown in FIG. 3(B), we observed a good correlation of particle coverage with concentration of target DNA in the range of 10 nM to 100 pM. FIG. 3 (A) through (D) shows the increasing coverage of magnetic nanoparticles with increased target DNA concentrations. The particles saturate the substrate above 10 nM and have low coverage below 100 pM. Over the tested concentration range, the assays shows good specificity with most nanoparticles only on the positive sensors and few nanoparticles or none nonspecifically adsorbed on the negative control sensors with control DNA probes (FIG. 3(E)); in addition, the nanoparticles did not aggregate and distributed uniformly, indicating a homogenous surface modification. The estimated nanoparticle coverage (in the number of captured nanoparticles per $\mu m^2$) versus the target concentration was plotted in FIG. 3(F).

Example 3

Magnetic Sensor Measurements

The success of the surface chemistry was further confirmed by real-time measurement of magnetic sensors. The two positive sensors were coated with 5'-5AmMC6/TTT TTT TTT TCT ACC AAT CCA CAA ATA CCC ATC TAC CAT A-3' (SEQ ID NO:4) probes, while the two control probes were coated with 5'-5AmMC6/TTT TTT TTT-3' (SEQ ID NO:2) probes. The positive probe sequence listed here can be seen to have a poly T spacer which will be adjacent the substrate and provides space for hybridization without interference by the substrate. The notation 5AmMC6 refers to a six-carbon linker and an amino group attached to the end. The DNA target used for hybridization was biotin5/5Biotin/TAT GGT AGA TCC GTA TTT GTG TTT GTG GAT TGG-3 (SEQ ID NO: 3) at a concentration of 10 nM. 5/5Biotin means that the biotin is attached to the 5' end of the oligo.

FIG. 4(A) shows a real time response of sensors by applying magnetic nanoparticle solution to a chip having hybridized with target DNA. This graph shows the voltage obtained over time, where the increased voltage results from biotinylated target binding of the nanoparticles coated with streptavidin (SA) in the proximity of a given spin valve sensor surface.

Figure 4:
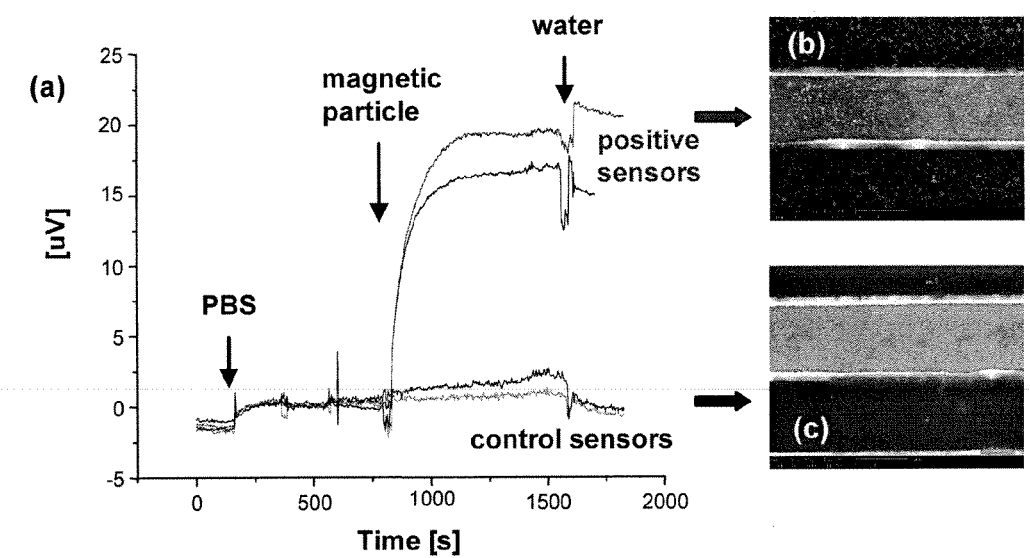
FIG. 4 (A) is a graph showing real-time responses of four magnetic sensors when buffer and magnetic nanoparticle solutions (MACS) are applied to a duplex DNA microarray.

Specific nanoparticle adsorption reached saturation in 10 minutes, characteristic of the strong affinity between biotin and SA. Also, the negative control sensor has a nearly flat non-zero signal (FIG. 4) that is most likely due to a drift effect of the sensor itself rather than nonspecific adsorption of target DNA. The initial jump when the chip was first exposed to buffer is due to the fact that the chip went from a dry condition to a wet condition. SEM images of nanoparticles on both positive and negative control sensors correspond well with the measurement results, with a high coverage of nanoparticles on positive sensor and close to zero coverage on negative control sensors (FIG. 4B-C). The slight difference in the signal amplitude between the two positive sensors is likely due to uneven DNA sample capture in our manual sample delivery protocol.

Example 4

Gold Surface

Gold surfaces are popular substrates for biomolecule immobilization, relying on the strong bond between thiol groups and gold. However, gold surfaces also require a strong acid or base cleaning to remove impurities; in addition, thiol-gold bonds are susceptible to oxidative desorption upon storage, resulting in a short shelf life (REF 9).

In this example, chemistry as described above was applied to a gold surface with a small modification. The gold surface was first coated with mercaptoundecanoic acid (MUA) followed with polyamine and polyacid coating. The gold substrate was obtained by coating a quartz substrate with a thin adhesion layer of Cr (2-3 nm), which facilitates the adhesion of a gold layer to quartz, and sputter depositing gold onto the coated quartz substrate. The final gold layer was about 100 nm. The gold substrate was immersed into a MUA in ethanol solution (1 mM) for 2 hours, and this step effectively introduced negative charges onto the gold substrate. Further modification of the gold surface with PAAm and PEMA followed the procedures described above. Briefly, the MUA-modified gold substrate was sequentially coated with PAAm and PEMA to form a bilayer. Positive and control oligonucleotide probes were then spotted on different areas followed by target hybridization and nanoparticle labeling.

After oligonucleotide probe immobilization and hybridization to complementary target DNA, the substrate was found to have similar nanoparticle coverage as that of $SiO_2$ substrate at the same target concentration. This observation indicates that this surface chemistry can indeed tolerate less-than-perfect activation of both gold and $SiO_2$ substrates for effectively immobilizing DNA probes with a high degree of probe coverage and excellent specificity in follow-on hybridization events.

CONCLUSION

The above specific description is meant to exemplify and illustrate the invention and should not be seen as limiting the scope of the invention, which is defined by the literal and equivalent scope of the appended claims. Any patents or publications mentioned in this specification are indicative of levels of those skilled in the art to which the patent pertains and are intended to convey details of the invention which may not be explicitly set out but which would be understood by workers in the field. Such patents or publications are hereby incorporated by reference to the same extent as if each was specifically and individually incorporated by reference, as needed for the purpose of describing and enabling the method or material referred to.

REFERENCES

1. Schena, M.; Heller, R. A.; Theriault, T. P.; Konrad, K.; Lachenmeier, E.; Davis, R. W. *Trends Biotechnol.* 1998, 16, 301-306.
2. Goldsmith, Z. G.; Dhanasekaran, N. *Int. J. Mol. Med.* 2004, 13, 483-495.
3. Voldman, J.; Gray, M. L.; Schmidt, M. A. *Annu. Rev. Biomed. Eng.* 1999, 1, 401-425.
4. Trau, D.; Jian, J.; and Nikoluas, S. J. *Langmuire* 2006, 22, 877-881.
5. Wang, S. X., White, R. L., Webb, C. D., and Li, G. "Magnetic nanoparticles, magnetic detector arrays, and methods for their use in detecting biological molecules," U.S. patent application Ser. No. 10/829,505, filed Apr. 22, 2004; Li, G.; Sun, S.; Wilson, R. J.; White, R. L.; Pourmand, N.; Wang, S. X. *Sens Actuators A* 2006, 126, 98-106.
6. Baselt, D. "Biosensor using magnetically-detected label." U.S. Pat. No. 5,981,297 issued Nov. 9, 1999; Miller, M. M.; Sheehan, P. E.; Edelstein, R. L.; Tamanaha, C. R.; Zhong, L.; Bounnak, S.; Whitman, L. J.; Colton, R. J. *J. Magn. Magn. Mater.* 2001, 225, 138-144.
7. Decher, G. *Science* 1997, 277, 1232-1237.
8. Gong, P.; Grainger, D. W. *Surf. Sci.* 2004, 570, 67-77.
9. Johnson, P. A.; Levicky, R. *Langmuir,* 2003, 19, 10288-10294.

What is claimed is:

1. A method for preparing a substrate for use in a biosensor, comprising:
   (a) providing a substrate surface which is reactive with an amine;
   (b) coating the substrate surface with a polyamine to form a polyamine covalently linked to the substrate; then
   (c) coating the polyamine covalently linked to the substrate with a polyacid anhydride having multiple acid anhydride groups to thereby form a layer of polyacid anhydride that binds to the polyamine covalently linked to the substrate with one portion of the multiple acid anhydride groups and retains another portion of the multiple acid anhydride groups for linking to amine groups on biomolecules, said polyacid anhydride coating comprising an at least partially hydrolyzed polyacid; then
   (d) dehydrating partially hydrolyzed polyacid to form a corresponding polyanhydride for linking to said amine groups on biomolecules.

2. The method of claim 1 where the substrate surface, which is reactive with an amine, comprises oxide groups.

3. The method of claim 2 where the oxide groups are selected from the group consisting of $SiO_2$, $Al_2O_3$, $Ta_2O_5$, and $TiO_2$.

4. The method of claim 1 where the substrate surface, which is reactive with an amine, comprises sulfide groups.

5. The method of claim 1 where the polyamine coating the substrate surface is a primary amine.

6. The method of claim 1 where the polyamine coating the substrate surface is selected from the group consisting of (3-aminopropyl)trimethoxysilane (APTMS) and N-(2- aminoethyl)-3-aminopropyl trimethoxysilane (EDA).

7. The method of claim 1 where the polyamine coating the substrate surface is a polyallylamine.

8. The method of claim 1 where the polyamine is selected from the group consisting of PEI (poly(ethyleneimine), PAAm (polyallylamine) and poly-L-lysine (PLL).

9. The method of claim 1 where the polyacid anhydride is a copolymer of a dicarboxylic acid anhydride and a monomer selected from the group consisting of ethylene, propylene, butene, butadiene, styrene, 1-octadecene and 1-tetradecene.

10. The method of claim 9 where the dicarboxylic acid anhydride is selected from the group consisting of fumaric acid, itaconic acid, maleic acid, maleic anhydride, chloromaleic acid, dimethyl fumarate, chloromaleic anhydride, and mixtures thereof.

11. The method of claim 1 where the polyacid anhydride comprises polyethylene and maleic acid.

12. The method of claim 1 where the polyacid anhydride is added in an aqueous solvent.

13. The method of claim 1 wherein the substrate surface is an oxide surface on silicon.

14. The method of claim 13 further comprising the step of patterning the substrate to expose a first portion of said polyamine covalently linked to the substrate that is contacted with said polyacid anhydride and to provide a second portion of said polyamine covalently linked to the substrate that is not contacted with said polyacid anhydride.

15. A method of preparing a biosensor, comprising the steps of:
   providing a substrate prepared in accordance with steps (a) through (d) of claim 1; then
   reacting the bonded polyacid anhydride with an amino-terminated biomolecule to link the biomolecule to the substrate.

16. The method of claim 15 further comprising the step of heating the substrate prior to reacting the bonded polyacid anhydride with the amino-terminated biomolecule.

17. The method of claim 15 where the biomolecule is selected from the group consisting of a polypeptide, a polynucleic acid, and a small molecule drug.

18. The method of claim 15 where the biomolecule is a polynucleic acid.

19. A method for preparing a biosensor, comprising:
   (a) providing a substrate having a surface reactive with a polyamine;
   (b) coating the substrate surface with the polyamine to provide a bonded polyamine;
   (c) forming multiple, physically discrete areas of exposed polyamine by patterning the substrate; and
   (d) layering polyacid anhydride on the exposed bonded polyamine.

20. The method of claim 19 where the polyacid anhydride is partially hydrolyzed and further comprising the step of dehydrating the partially hydrolyzed polyacid anhydride to a corresponding polyanhydride.

21. The method of claim 19 further comprising the step of reacting the polyacid anhydride with a plurality of different species of amino-terminated biomolecules, wherein the reacting causes different species of biomolecules to link to different physically discrete areas of the substrate.

22. A biosensor, comprising:
   (a) a substrate;
   (b) a polyamine layer on the substrate;
   (c) a patterned layer on the polyamine layer which defines separate, discrete physical areas of exposed polyamine in the polyamine layer;

(d) a polyanhydride layer on each discrete physical area of the exposed polyamine in the polyamine layer; and (e) a plurality of probe biomolecules attached to the polyanhydride layer through an amine group on the biomolecule, where the probe biomolecules are attached as different populations in each discrete physical area of the polyanhydride layer.

23. The biosensor of claim 22 where the substrate has magnetic properties.

24. The biosensor of claim 22 where the substrate comprises a magnetoresistive layer.

25. The biosensor of claim 24 further comprising electrical connections to discrete physical areas of the substrate for measuring changes in resistance due to binding of a magnetic target molecule to a probe biomolecule.

26. The biosensor of claim 25 further comprising instrumentation for measuring changes in resistance in each discrete physical area.

* * * * *

UNITED STATES PATENT AND TRADEMARK OFFICE
CERTIFICATE OF CORRECTION

PATENT NO. : 7,989,396 B2
APPLICATION NO. : 11/949442
DATED : August 2, 2011
INVENTOR(S) : Heng Yu et al.

Page 1 of 1

It is certified that error appears in the above-identified patent and that said Letters Patent is hereby corrected as shown below:

Column 1, line 14, "POI-HG00025" should read --POI-HG000205--

Signed and Sealed this
Twenty-fourth Day of July, 2012

David J. Kappos
*Director of the United States Patent and Trademark Office*

SEQUENCE LISTING

```
<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: oligonucleotide

<400> SEQUENCE: 1
ctaccaatcc acaaataccc atctaccata                                        30

<210> SEQ ID NO 2
<211> LENGTH: 12
<212> TYPE: DNA
<213> ORGANISM: Artificial Sequence
<220> FEATURE:
<223> OTHER INFORMATION: oligonucleotide

<400> SEQUENCE: 2
tttttttttt tt                                                           12

<210> SEQ ID NO 3
<211> LENGTH: 27
<212> TYPE: DNA
<213> ORGANISM: Artificial Sequence
<220> FEATURE:
```

-continued

```
<223> OTHER INFORMATION: oligonucleotide

<400> SEQUENCE: 3
tatggtagat gggtatttgt ggattgg                                      27

<210> SEQ ID NO 4
<211> LENGTH: 39
<212> TYPE: DNA
<213> ORGANISM: Artificial Sequence
<220> FEATURE:
<223> OTHER INFORMATION: oligonucleotide

<400> SEQUENCE: 4
tttttttttt ctaccaatcc acaaataccc atctaccat                         39
```